US00PP18309P2

(12) United States Plant Patent
Meszaros

(10) Patent No.: US PP18,309 P2
(45) Date of Patent: Dec. 11, 2007

(54) *PETUNIA* PLANT NAMED 'PET0605'

(50) Latin Name: *Petunia×hybrida*
Varietal Denomination: PET0605

(75) Inventor: Debra Meszaros, Riverhead, NY (US)

(73) Assignee: Advanced Plant Technologies LLC, Riverhead, NY (US)

( * ) Notice: Subject to any disclaimer, the term of this patent is extended or adjusted under 35 U.S.C. 154(b) by 0 days.

(21) Appl. No.: 11/436,836

(22) Filed: May 18, 2006

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP16,786 P2 * 7/2006 Iwaki et al. ..... Plt./356

* cited by examiner

*Primary Examiner*—Wendy C. Haas

(57) ABSTRACT

A new and distinct cultivar of *Petunia* plant named 'PET0605', characterized by its mounding, outwardly spreading, compact plant habit; freely branching compact growth habit; green foliage; and lavender flower with purple venation.

2 Drawing Sheets

Botanical designation: *Petunia×hybrida.*
Cultivar denomination: 'PET0605'.

CROSS REFERENCE TO RELATED APPLICATIONS

The claimed plant is related to 'PET0602', the subject of co-pending U.S. Plant patent application Ser. No. 11/436,834 and 'PET0610', the subject of co-pending U.S. Plant patent application Ser. No. 11/436,842 in that each plant has the same parentage.

BACKGROUND OF THE INVENTION

The present Invention relates to a new and distinct cultivar of *Petunia* plant, botanically known as *Petunia×hybrida,* and hereinafter referred to by the cultivar name 'PET0605'.

The new *Petunia* originated from a conventional cross of proprietary *Petunia* selections, 'Glam' (The female parent; not patented) and 'PET0482' (the male parent; not patented) conducted on the 2$^{nd}$ day of May 2004 in a cultivated area of Aquebogue, N.Y. Seeds from this cross were planted and the individual plant known as 'PET0605' was selected because of its combination of exceptional features, and has been propagated asexually by vegetative cuttings since that time. The unique features of this new *Petunia* are stable and reproduced true to type in successive generations.

SUMMARY OF THE INVENTION

Plants of the cultivar 'PET0605' have not been observed under all possible environmental conditions. The phenotype may vary somewhat with variations in environment such as temperature and light intensity without, however, any variance in genotype.

The following traits have been repeatedly observed and are determined to be the unique characteristics of 'PET0605'. These characteristics in combination distinguish 'PET0605' as a new and distinct cultivar:

1. Compact, mounding and outwardly spreading plant habit.
2. Freely branching growth habit with short internode spacing.
3. Flower color.
4. Ability to tolerate rainy weather conditions.

Plants of the new *Petunia* differ from the parent plants in plant growth and tolerance to rain.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which accurately describe the colors of the new *Petunia.*

The photograph on the first sheet comprises a side perspective view of a typical flowering plant of 'PET0605' grown in a container.

The photograph on the second sheet comprises a close-up view of typical leaves and flowers of 'PET0605'.

DETAILED BOTANICAL DESCRIPTION

The aforementioned photographs and following observations and measurements describe plants grown in Aquebogue, N.Y., under commercial practice during the spring and summer in a polyethylene covered greenhouse with day temperatures averaging 22 degrees C., night temperatures averaging 17 degrees C., and light levels ranging from 9,000 to 12,000 lux. Plants were grown for about 16 weeks in 25 cm containers. In the following description, color references are made to The Royal Horticultural Society Colour Chart, 2001 Edition, except where general terms of ordinary dictionary significance are used.

Botanical classification: *Petunia×hybrida* cultivar 'PET0605'.

*Parentage.*—Female: 'Glam', Male: 'PET0482'.

Propagation:

*Type cutting.*—Vegetative cuttings.

*Time to initiate roots, summer.*—About 15 days.

*Time to initiate roots, winter.*—About 20 days.

*Time to produce a rooted young plant, summer.*—About three weeks.

*Time to produce a rooted young plant, winter.*—About four weeks.

*Root description.*—Fine, fibrous; white in color.

*Rooting habit.*—Freely branching, dense.

Plant description:

*Form.*—Annual flowering plant; indeterminate; initially upright, then mounding and outwardly spreading; compact growth habit. Freely basal branching habit lateral branches potentially developing at every node.

*Usage.*—Appropriate for hanging baskets, window boxes, patio containers and landscape applications.

*Plant height.*—About 25 cm.

*Plant diameter.*—About 50 cm.

Lateral branches:

*Length.*—About 20–25 cm.

*Diameter.*—About 3 mm.

*Internode length.*—About 2 cm.

*Texture.*—Pubescent.

*Color.*—143A.

Foliage description:

*Arrangement, before flowering.*—Alternate, simple.

*Arrangement, when flowering.*—Opposite, simple.

*Length.*—About 3.5 cm.

*Width.*—About 2.0 cm.

*Shape.*—Ovate.

*Apex.*—Acute.

*Base.*—Obtuse.

*Margin.*—Entire.

*Texture, upper and lower surfaces.*—Viscid, pubescent.

*Venation pattern.*—Pinnate, arcuate.

*Color.*—Developing foliage, upper surface: 137A. Developing foliage, lower surface: 137C. Fully expanded foliage, upper surface: 137A. Fully expanded foliage, lower surface: 137C. Venation, upper and lower surfaces: Similar to lamina. Petiole length: About 3 mm. Petiole diameter: About 2 mm. Petiole texture, upper and lower surfaces: Pubescent. Petiole color, upper and lower surfaces: 137A.

Flower description:

*Flower type and habit.*—Salverform flowers; flowers face upward or outward; single, axillary. Freely flowering, typically about ten open flowers and flower buds per lateral branch.

*Natural flowering season.*—Not day length responsive; plants flower from April until frost in New York; flowering continuous during the flowering period. Plants start flowering about three weeks after planting.

*Flower longevity on the plant.*—About one week; flowers not persistent.

*Fragrance.*—None detected.

*Flower size.*—Diameter: About 6 cm. Depth: About 6 cm. Tube length: About 3.5 cm. Throat diameter, distal end: About 1.3 cm. Tube diameter, proximal end: About 3 mm.

*Flower buds.*—Length: About 4.8 cm. Diameter: About 6 mm. Shape: Elongated oblong with ruffled apices. Color: 86A.

*Corolla.*—Arrangement/appearance: Single whorl of five petals, fused into flared trumpet with distinct clefts between petal lobes. Petal lobe length: About 3 cm. Petal lobe width: About 3 cm. Petal shape: Roughly fan-shaped. Petal apex: Acute. Petal margin: Entire. Petal texture, upper surface: Smooth, satiny. Petal texture, lower surface: Pubescent. Petal, when opening, upper surface: 77C. Petal, when opening, lower surface: 77D. Petal, fully opened, upper surface: N78B. Petal, fully opened, lower surface: N78C. Flower throat (inside): 79B. Flower tube (outside): 79B. Venation, upper petal surface: N78A. Venation, lower petal surface: N78A. Venation, throat: N78A. Venation, tube: 79B.

*Sepals.*—Arrangement/appearance: Single whorl of five sepals fused at base, star-shaped. Length: About 3 cm. Width: About 2.8 cm. Shape: Linear. Apex: Acute. Margin: Entire. Texture, upper and lower surfaces: Pubescent. Color, upper and lower surfaces: N78B.

*Peduncles.*—Length: About 3.6 cm. Width: About 2 mm. Angle: About 45 degrees to the stem. Strength: Strong. Texture: Pubescent. Color: 143A.

*Reproductive organs.*—Stamens: Quantity/arrangement: Five per flower; stamens adnate to corolla tube. Anther shape: Oval. Anther length: About 1.5 m. Anther color: 93C. Pollen amount: Moderate. Pollen color: 93C. Pistils: Quantity: One per flower. Pistil length: About 1.8 cm. Stigma shape: Rounded. Stigma color: 150B. Style length: About 1.6 cm. Style color: 141C. Ovary color: 144B. Fruit/seed: Fruit and seed production has not been observed.

Disease/pest resistance: Plants of the new *Petunia* have not been noted to be resistant to pathogens and pests common to *Petunia*.

Temperature tolerance: Plants of the new *Petunia* have been observed to tolerate temperatures ranging from 2 to 32 degrees C.

What is claimed is:

1. A new and distinct cultivar of *Petunia* plant named 'PET0605', as illustrated and described.

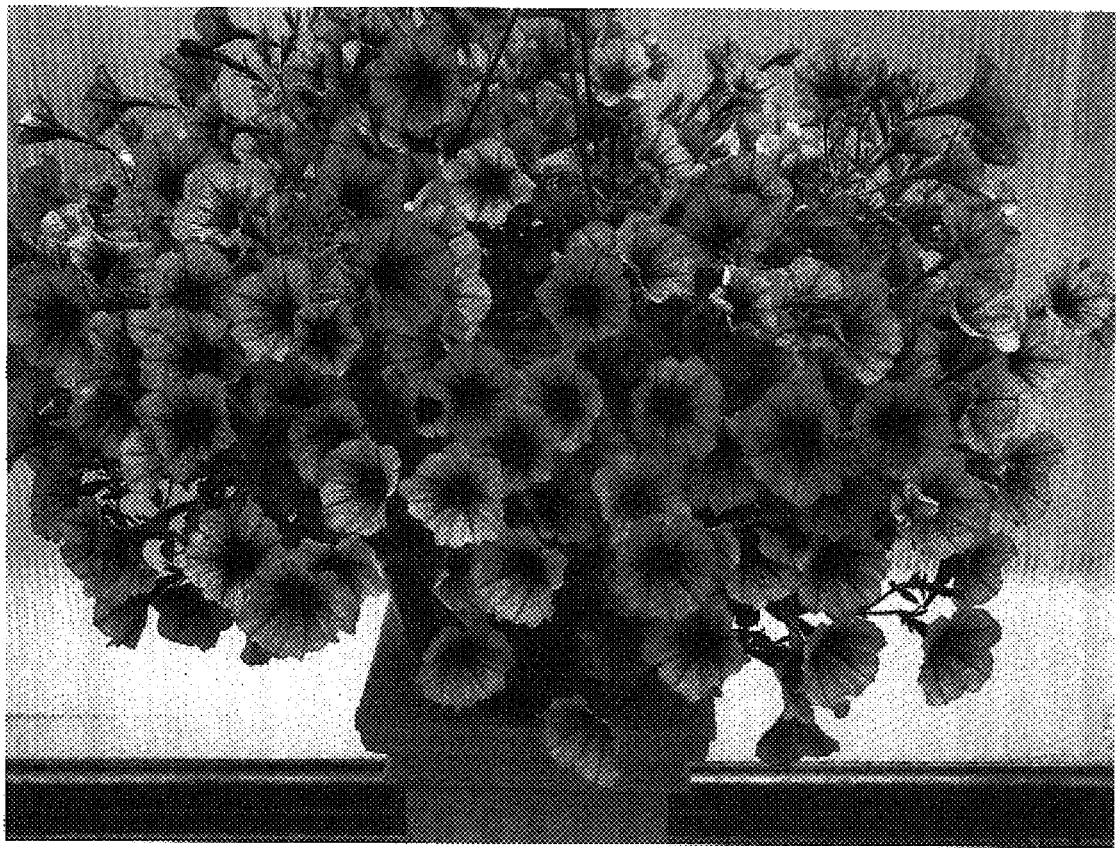

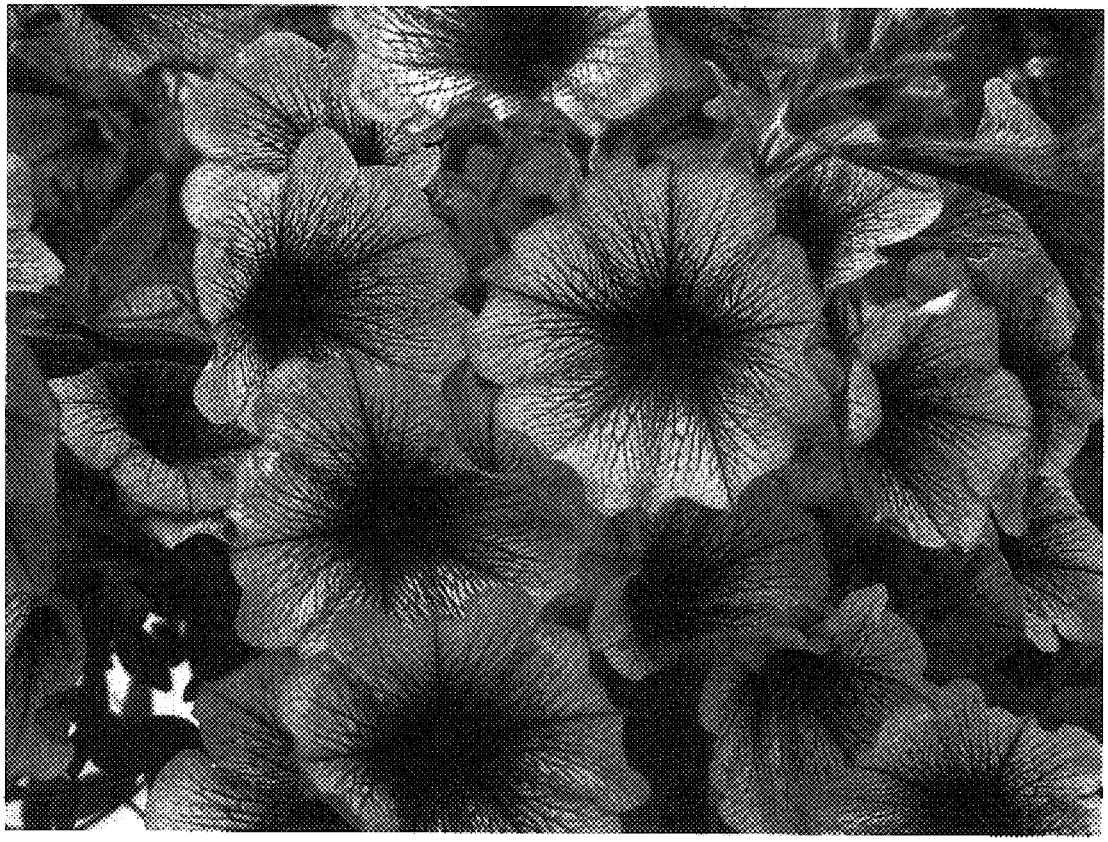

* * * * *